(12) United States Patent
Uchio et al.

(10) Patent No.: US 11,931,396 B2
(45) Date of Patent: Mar. 19, 2024

(54) COMPOSITION FOR IMPROVING VASCULAR ENDOTHELIAL FUNCTION OR IMPROVING BLOOD FLOW IN PERIPHERAL BLOOD VESSELS

(71) Applicant: House Wellness Foods Corporation, Hyogo (JP)

(72) Inventors: Ryusei Uchio, Itami (JP); Koutarou Muroyama, Itami (JP); Kengo Kawasaki, Itami (JP); Shinji Murosaki, Itami (JP)

(73) Assignee: HOUSE WELLNESS FOODS CORPORATION, Hyogo (JP)

( * ) Notice: Subject to any disclaimer, the term of this patent is extended or adjusted under 35 U.S.C. 154(b) by 0 days.

(21) Appl. No.: 17/710,293

(22) Filed: Mar. 31, 2022

(65) Prior Publication Data

US 2022/0218780 A1 Jul. 14, 2022

Related U.S. Application Data

(62) Division of application No. 17/252,433, filed as application No. PCT/JP2019/025705 on Jun. 27, 2019, now abandoned.

(30) Foreign Application Priority Data

Jun. 29, 2018 (JP) .................................. 2018-125052

(51) Int. Cl.
| | |
|---|---|
| *A61K 36/00* | (2006.01) |
| *A23L 33/105* | (2016.01) |
| *A61K 31/12* | (2006.01) |
| *A61K 36/9066* | (2006.01) |

(52) U.S. Cl.
CPC ........ *A61K 36/9066* (2013.01); *A23L 33/105* (2016.08); *A61K 31/12* (2013.01); *A61K 2236/331* (2013.01)

(58) Field of Classification Search
CPC ..................................... A61P 9/00; A61P 9/10
See application file for complete search history.

(56) References Cited

U.S. PATENT DOCUMENTS

2008/0193573 A1* 8/2008 Gow ........................ A61P 25/28
426/655

FOREIGN PATENT DOCUMENTS

| CN | 101703745 B | * | 7/2011 |
| CN | 105194558 A | * | 12/2015 |
| JP | H10-194938 A | | 7/1998 |
| JP | 2009-530305 A | | 8/2009 |
| JP | 2012-236826 A | | 12/2012 |
| JP | 2015-143200 A | | 8/2015 |
| JP | 2016-044169 A | | 4/2016 |

OTHER PUBLICATIONS

Sun et al, Bisacurone inhibits adhesion of inflammatory monocytes or cancer cells to endothelial cells through down-regulation of VCAM-1 expression. International Immunopharmacology, (Sep. 2008) vol. 8, No. 9, pp. 1272-1281 (Year: 2008).*
Uchio et al., "A hot wwater extract of tumeric (*Cucuma longa*) suppresses acute ethanol-induced liver injury in mice by inhibiting hepatic oxidative stress and inflammatory cytokine production," Journal of Nutritional Science, 6 (2017).
Office Action issued in related U.S. Appl. No. 17/252,433 dated Mar. 29, 2022.
Uchio et al., "A hot water extract of tumeric (*Curcuma longa*) suppresses acute ethanol-induced liver injury in mice by inhibiting hepatic oxidative stress and inflammatory cytokine production," Journal of Nutritional Science, 6 (2017) ISSN: 2048-6790.
Sugiyama, "Reactive Hyperemia Peripheral Vascular endothelial function assessment by arterial tonometry (RH-PAT)," Heart's Selection 3, 46 (10): 1330-1335 (2014).
Adaramoye et al., "Hypotensive and endothelium-independent vasorelaxant effects of methanolic extract from *Curcuma longa* L. in rats," Journal of Ethnopharmacology, 124 (3): 457-462 (2009).
Adaramoye et al., "Involvement of Na+—Ca2+ exchanger in the endothelium-independent vasorelaxation induced by *Curcuma longa* L. in isolated rat superior mesenteric arteries," Journal of Smooth Muscle Research, 44 (5): 151-158 (2008).
Ashraf et al., "Antiatherosclerotic effects of dietary supplementations of garlic and turmeric: Restoration of endothelial function in rats," Life Sciences, 77: 837-857 (2005).
Rungseesantivanon et al., "Curcumin supplementation could improve diabetes-induced endothelial dysfunction associated with decreased vascular superoxide production and PKC inhibition," BMC Complementary & Alternative Medicine, 10: 57 (2010).
Morooka et al., "Evolution of vascular endothelial function studies," The Journal of the Japanese Society of Internal Medicine, 106 (4): 850-857 (2017).
Ogata et al., "On the Physiological Mechanisms of Cold Disease—Evaluation by hemodynamic and autonomic nerve activity indices," Japanese Journal of Nursing Art and Science, 15 (3): 227-234 (2017).
Ushiroyama, "Clinical Analysis of Pathologic Conditions of Sensitivity to Cold and Correspondence, What pathologic conditions sensitivity to cold has? How can sensitivity to cold be treated?," Medical History, 215 (11): 925-929(2005).
International Search Report issued in corresponding International Patent Application No. PCT/JP2019/025705 dated Sep. 17, 2019.
Initial Study of Turmeric and Turmeric's Activating Blood Action and Medicinal Cold Temperature in OHLEO, Stage 07, 21-22, pp. 32-34 (Dec. 31, 2009).
"Muscle Relaxation Drugs," Daisho, p. 53, Shanghai World Book Publishing Co., Ltd. (Jun. 30, 2015) (see CN OA translation).

(Continued)

*Primary Examiner* — Qiuwen Mi
(74) *Attorney, Agent, or Firm* — Morgan, Lewis & Bockius LLP

(57) ABSTRACT

The present disclosure provides a composition for improving vascular endothelial function or improving blood flow in peripheral blood vessels, comprising, as an active ingredient, an ingredient derived from a turmeric.

5 Claims, 2 Drawing Sheets

(56) References Cited

OTHER PUBLICATIONS

Fujian Local Pharmaceutical Contemporary Research, Zhuang Yuan et al., p. 153, Fujian Science and Technology Publishing Co., Ltd. (Oct. 31, 2014) (see CN OA translation).
Office Action issued in corresponding Chinese Patent Application No. 201980042798.7 dated Nov. 29, 2021.
"Meta double," Yao Medicine Forum Medical Database Center, <<https://web.archive.org/web/20170721011132/https://www.med126.com/mingzu/2009/20090512123050_154752.shtml>> (Jul. 21, 2017).
Kawasaki et al., "A hot water extract of Curcuma longa inhibits adhesion molecule protein expression and monocyte adhesion to TNF-α-stimulated human endothelial cells," Bioscience, Biotechnology, and Biochemistry, 79(10): 1654-1659 (2015).
"Health Sharing—Three Tips to Improve Cold Hands and Feet in Women," Parent-Child World Magazine <<yogajourney.com.tw/health-news-5/?lang=en>> (Dec. 18, 2014).
Japanese Office Action dated Sep. 19, 2023 issued in Japanese Patent Application No. 2020-527658.

\* cited by examiner

COMPOSITION FOR IMPROVING VASCULAR ENDOTHELIAL FUNCTION OR IMPROVING BLOOD FLOW IN PERIPHERAL BLOOD VESSELS

TECHNICAL FIELD

The present invention relates to a composition for improving vascular endothelial function or improving blood flow in peripheral blood vessels.

BACKGROUND ART

Vascular endothelial cells are cells that cover the vascular lumen, and the cells play a role for regulating contraction/dilation of blood vessels, blood coagulation, inflammation, angiogenesis, and the like. It has been revealed that unbalanced diet (i.e., high fat diet, smoking, lack of exercise, etc.), obesity, hypertension, hyperlipidemia, hyperglycemia, and the like cause to damage endothelial cells and to decrease vascular endothelial function. In addition, it has been known that a reduction in vascular endothelial function induces progression of arteriosclerosis, vulnerable plaque formation, and macroangiopathy, and that if such a reduction in vascular endothelial function further progresses, it causes circulatory diseases (angina, myocardial infarction, stroke, etc.). Thus, the maintenance or improvement of vascular endothelial function is important for prevention of various circulatory diseases (Non Patent Literatures 1 and 2).

On the other hand, it has been known that a turmeric comprises a large number of physiologically active substances.

Non Patent Literatures 3 and 4 disclose that a methanol extract of autumn turmeric extract was used as a specimen in an experiment, a mesenteric artery (blood vessel) collected from a rat was added into a buffer, and the turmeric specimen was then added into the buffer, so that the blood vessel was dilated.

Non Patent Literature 5 discloses that vasodilator capacity was improved in rats fed with a feed comprising an autumn turmeric and a garlic.

Non Patent Literature 6 discloses a reduction in vascular endothelial function associated with diabetes was improved in diabetes rat models by continuous administration of curcumin. Non Patent Literature 6 describes that curcumin was administered to diabetes rat models every day via oral intake at a daily dose of 30 mg/kg body weight and 300 mg/kg body weight.

Patent Literature 1 discloses a vascular endothelial function improving agent comprising, as active ingredients, a clove, a coriander, a cumin, a garlic, a ginger, an onion, a red pepper, and a turmeric.

Moreover, it has been considered that peripheral blood flow disorder occurs due to angiopathy caused by various pathologic conditions such as arteriosclerosis, and such peripheral blood flow disorder has been known as a cause of sensitivity to cold. In a study targeting 3000 or more female subjects, it has been reported that 50% or more of female subjects over 55 years old had realized sensitivity to cold (Non Patent Literatures 7 and 8). Since such sensitivity to cold is often attended with symptoms such as insomnia, stiff shoulders and constipation (Non Patent Literature 7), the improvement of blood flow is important for the improvement of QOL.

CITATION LIST

Patent Literature

Patent Literature 1: JP 2016-044169 A

Non Patent Literature

Non Patent Literature 1: Toshifumi MOROOKA, Koichi NODE. Progression of Studies regarding Vascular Endothelial Function. The Journal of the Japanese Society of Internal Medicine, Vol. 106, No. 4, 2017.
Non Patent Literature 2: Seigo SUGIYAMA. Evaluation of vascular endothelial function by reactive hyperemia peripheral arterial tonometry (RH-PAT). Heart, Vol. 46, No. 10, 2014.
Non Patent Literature 3: J Ethnopharmacol. 2009 Jul. 30; 124(3): 457-62.
Non Patent Literature 4: J Smooth Muscle Res. 2008 October; 44(5): 151-8.
Non Patent Literature 5: Life Sci. 2005 Jul. 8; 77(8): 837-57.
Non Patent Literature 6: BMC Complementary and Alternative Medicine 2010, 10: 57.
Non Patent Literature 7: Yu OGATA, Kentaro KANEKO, Keita GOTO, Kaori KAWANO, Machiko YAMAMOTO, Keita GOTO (2017). Regarding Physiological Mechanism of Sensitivity to Cold, Evaluation with Circulatory Dynamics and Autonomic Nerve Activity Indexes, Japanese Journal of Nursing Art and Science Vol. 15 (3), pp. 227-234, 2017.
Non Patent Literature 8: Naohisa ATOYAMA, Clinical Analysis of Pathologic Conditions of Sensitivity to Cold and Correspondence, What pathologic conditions sensitivity to cold has? How can sensitivity to cold be treated? Progress of Medicine, 215(11), 925-929 (2005).

SUMMARY OF INVENTION

Technical Problem

The present invention provides a composition that is effective for improving vascular endothelial function.

The present invention also provides a composition that is effective for improving blood flow in peripheral blood vessels.

Solution to Problem

The present inventors have found that vasodilator capacity is significantly improved in a human who has ingested a tablet comprising a turmeric extract containing turmeronol A, turmeronol B and bisacurone every day for 12 weeks, and that cold extremities are also improved in such a human. This has led to the completion of the present invention described below.

(1) A composition for improving vascular endothelial function or improving blood flow in peripheral blood vessels, comprising, as an active ingredient, at least one of turmeronol A, turmeronol B and bisacurone.
(2) The composition for improving vascular endothelial function or improving blood flow in peripheral blood vessels according to the above (1), comprising a turmeric extract extracted with at least one extraction solvent selected from water and a hydrophilic organic solvent, the turmeric extract comprising the at least one of turmeronol A, turmeronol B and bisacurone.

(3) A composition for improving vascular endothelial function or improving blood flow in peripheral blood vessels, comprising, as an active ingredient, a turmeric extract extracted with at least one extraction solvent selected from water and a hydrophilic organic solvent, the turmeric extract comprising at least one of turmeronol A, turmeronol B and bisacurone.
(4) The composition for improving vascular endothelial function or improving blood flow in peripheral blood vessels according to any one of the above (1) to (3), comprising 20 μg or more turmeronol A and turmeronol B in total per daily intake.
(5) The composition for improving vascular endothelial function or improving blood flow in peripheral blood vessels according to any one of the above (1) to (4), comprising 17 μg or more turmeronol A per daily intake.
(6) The composition for improving vascular endothelial function or improving blood flow in peripheral blood vessels according to any one of the above (1) to (5), comprising 5 μg or more turmeronol B per daily intake.
(7) The composition for improving vascular endothelial function or improving blood flow in peripheral blood vessels according to any one of the above (1) to (6), comprising 80 μg or more bisacurone per daily intake.
(8) The composition for improving vascular endothelial function or improving blood flow in peripheral blood vessels according to any one of the above (1) to (7), wherein the content of curcumin is less than 30 mg per daily intake.
(9) A composition for improving vascular endothelial function or improving blood flow in peripheral blood vessels, comprising a turmeric as an active ingredient, wherein the composition does not further comprise a clove, a coriander, a cumin, a garlic, a ginger, an onion and a red pepper, and the composition does not further comprise a garlic.
(10) Use of at least one of turmeronol A, turmeronol B and bisacurone, or a turmeric extract extracted with at least one extraction solvent selected from water and a hydrophilic organic solvent, the turmeric extract comprising at least one of turmeronol A, turmeronol B and bisacurone, for production of a composition for improving vascular endothelial function.
(11) Use of at least one of turmeronol A, turmeronol B and bisacurone, or a turmeric extract extracted with at least one extraction solvent selected from water and a hydrophilic organic solvent, the turmeric extract comprising at least one of turmeronol A, turmeronol B and bisacurone, for production of a medicament for improving vascular endothelial function.

The above-described composition or medicament for improving vascular endothelial function preferably comprises 20 μg or more turmeronol A and turmeronol B in total per daily intake. The above-described composition or medicament for improving vascular endothelial function preferably comprises 17 μg or more turmeronol A per daily intake. The above-described composition or medicament for improving vascular endothelial function preferably comprises 5 μg or more turmeronol B per daily intake. The above-described composition or medicament for improving vascular endothelial function preferably comprises 80 μg or more bisacurone per daily intake. In the above-described composition or medicament for improving vascular endothelial function, the content of curcumin is preferably less than 30 mg per daily intake.
(12) A method for improving vascular endothelial function, comprising:
administering at least one of turmeronol A, turmeronol B and bisacurone, or a turmeric extract extracted with at least one extraction solvent selected from water and a hydrophilic organic solvent, the turmeric extract comprising at least one of turmeronol A, turmeronol B and bisacurone, to a subject in need of improving vascular endothelial function; and
improving the vascular endothelial function in the subject.
(13) At least one of turmeronol A, turmeronol B and bisacurone, or a turmeric extract extracted with at least one extraction solvent selected from water and a hydrophilic organic solvent, the turmeric extract comprising at least one of turmeronol A, turmeronol B and bisacurone, which is for use in improving vascular endothelial function in a subject in need of improving the vascular endothelial function.

The active compound or the turmeric extract according to the above (13) is administered to the above-described subject, preferably, at a daily dose of 20 μg or more turmeronol A and turmeronol B in total, so as to improve the vascular endothelial function in the subject. The active compound or the turmeric extract according to the above (13) is administered to the above-described subject, preferably, at a daily dose of 17 μg or more turmeronol A, so as to improve the vascular endothelial function in the subject. The active compound or the turmeric extract according to the above (13) is administered to the above-described subject, preferably, at a daily dose of 5 μg or more turmeronol B, so as to improve the vascular endothelial function in the subject. The active compound or the turmeric extract according to the above (13) is administered to the above-described subject, preferably, at a daily dose of 80 μg or more bisacurone, so as to improve the vascular endothelial function in the subject. The active compound or the turmeric extract according to the above (13) is administered to the above-described subject, preferably, at a daily dose of less than 30 mg of curcumin, so as to improve the vascular endothelial function in the subject.
(14) Use of a turmeric for production of a composition for improving vascular endothelial function.
(15) Use of a turmeric for production of a medicament for improving vascular endothelial function.
(16) A method for improving vascular endothelial function, comprising:
administering a turmeric to a subject in need of improving vascular endothelial function; and
improving the vascular endothelial function in the subject.
(17) A turmeric for use in improving vascular endothelial function in a subject in need of improving the vascular endothelial function.

In the above (14) to (17), the above-described turmeric is neither a combination of a turmeric with a clove, a coriander, a cumin, a garlic, a ginger, an onion and a red pepper, nor a combination of a turmeric with a garlic.
(18) Use of at least one of turmeronol A, turmeronol B and bisacurone, or a turmeric extract extracted with at least one extraction solvent selected from water and a hydrophilic organic solvent, the turmeric extract comprising at least one of turmeronol A, turmeronol B and bisacurone, for production of a composition for improving blood flow in peripheral blood vessels.
(19) Use of at least one of turmeronol A, turmeronol B and bisacurone, or a turmeric extract extracted with at least one extraction solvent selected from water and a hydrophilic organic solvent, the turmeric extract comprising at least one of turmeronol A, turmeronol B and bisacurone, for production of a medicament for improving blood flow in peripheral blood vessels.

The above-described composition or medicament for improving blood flow in peripheral blood vessels preferably comprises 20 μg or more turmeronol A and turmeronol B in total per daily intake. The above-described composition or medicament for improving blood flow in peripheral blood vessels preferably comprises 17 µg or more turmeronol A per daily intake. The above-described composition or medicament for improving blood flow in peripheral blood vessels preferably comprises 5 µg or more turmeronol B per daily intake. The above-described composition or medicament for improving blood flow in peripheral blood vessels preferably comprises 80 µg or more bisacurone per daily intake. In the above-described composition or medicament for improving blood flow in peripheral blood vessels, the content of curcumin is preferably less than 30 mg per daily intake.

(20) A method for improving blood flow in peripheral blood vessels, comprising:

administering at least one of turmeronol A, turmeronol B and bisacurone, or a turmeric extract extracted with at least one extraction solvent selected from water and a hydrophilic organic solvent, the turmeric extract comprising at least one of turmeronol A, turmeronol B and bisacurone, to a subject in need of improving blood flow in peripheral blood vessels; and improving the blood flow in peripheral blood vessels in the subject.

(21) At least one of turmeronol A, turmeronol B and bisacurone, or a turmeric extract extracted with at least one extraction solvent selected from water and a hydrophilic organic solvent, the turmeric extract comprising at least one of turmeronol A, turmeronol B and bisacurone, which is for use in improving blood flow in peripheral blood vessels in a subject in need of improving the blood flow in peripheral blood vessels.

The active compound or the turmeric extract according to the above (21) is administered to the above-described subject, preferably, at a daily dose of 20 µg or more turmeronol A and turmeronol B in total, so as to improve the blood flow in peripheral blood vessels in the subject. The active compound or the turmeric extract according to the above (21) is administered to the above-described subject, preferably, at a daily dose of 17 µg or more turmeronol A, so as to improve the blood flow in peripheral blood vessels in the subject. The active compound or the turmeric extract according to the above (21) is administered to the above-described subject, preferably, at a daily dose of 5 µg or more turmeronol B, so as to improve the blood flow in peripheral blood vessels in the subject. The active compound or the turmeric extract according to the above (21) is administered to the above-described subject, preferably, at a daily dose of 80 µg or more bisacurone, so as to improve the blood flow in peripheral blood vessels in the subject. The active compound or the turmeric extract according to the above (21) is administered to the above-described subject, preferably, at a daily dose of less than 30 mg of curcumin, so as to improve the blood flow in peripheral blood vessels in the subject.

(22) Use of a turmeric for production of a composition for improving blood flow in peripheral blood vessels.

(23) Use of a turmeric for production of a medicament for improving blood flow in peripheral blood vessels.

(24) A method for improving blood flow in peripheral blood vessels, comprising:

administering a turmeric to a subject in need of improving blood flow in peripheral blood vessels; and improving the blood flow in peripheral blood vessels in the subject.

(25) A turmeric for improving blood flow in peripheral blood vessels in a subject in need of improving the blood flow in peripheral blood vessels.

In the above (22) to (25), the above-described turmeric is neither a combination of a turmeric with a clove, a coriander, a cumin, a garlic, a ginger, an onion and a red pepper, nor a combination of a turmeric with a garlic.

This description contains part or all of the content as disclosed in the description and/or drawings of Japanese Patent Application No. 2018-125052, based on which the present application claims a priority.

Advantageous Effects of Invention

The present invention provides a composition for improving vascular endothelial function and a composition for improving blood flow in peripheral blood vessels.

DESCRIPTION OF EMBODIMENTS

<Turmeric>

Figure 1:
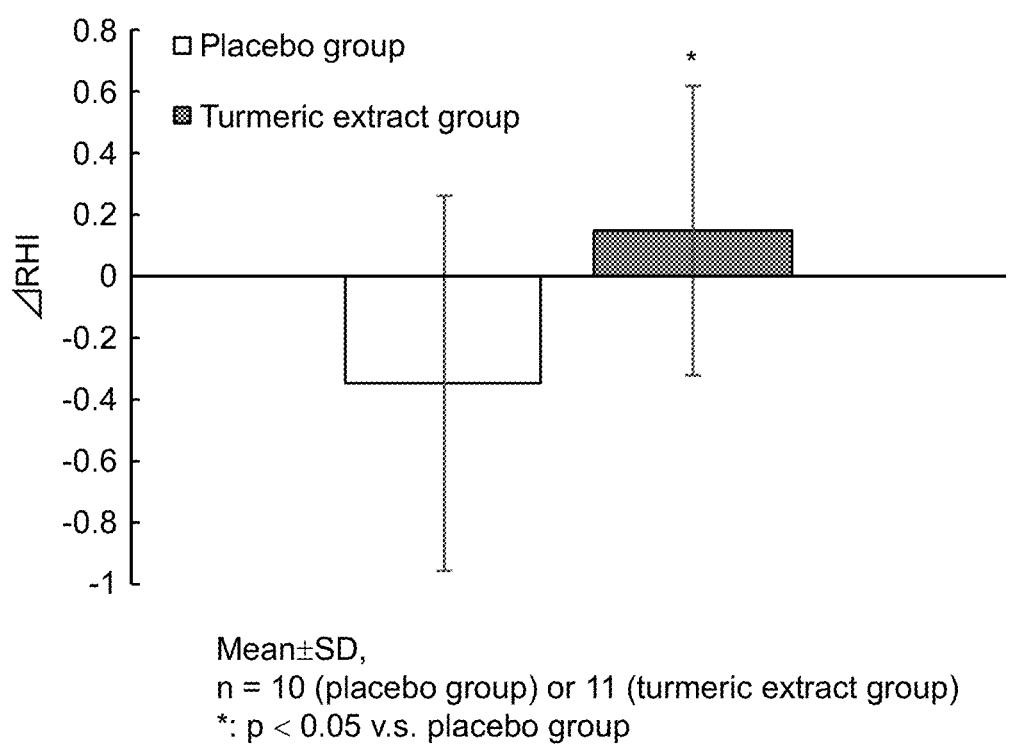
FIG. 1 shows the amount of change (ΔRHI) in the vascular endothelial function (RHI) from before the intake of a test food (a turmeric extract group or a placebo group) to 12 weeks after the intake of the test food.

In the present invention, the term "turmeric" indicates a plant belonging to Zingiberaceae, genus *Curcuma*. Specific examples of the turmeric may include *Curcuma longa* (autumn turmeric), *Curcuma aromatica, Curcuma zedoaria, Curcuma phaeocaulis, Curcuma kwangsiensis, Curcuma wenyujin*, and/or *Curcuma xanthorrhiza*. Among these, *Curcuma longa* is particularly preferable.

In the present invention, as such a turmeric, a turmeric portion including a rhizome is preferably used The shape of the turmeric used in the present invention is not particularly limited, and thus, the turmeric may be a crushed product, a squeezed juice or an extract of turmeric, or a processed product thereof. The turmeric used in the present invention is particularly preferably a turmeric extract. Hereafter, preferred embodiments of the turmeric extract will be described.

<Turmeric Extract>

In the present invention, the term "turmeric extract" refers to an extract of a plant material derived from a plant of the genus *Curcuma* in the family Zingiberaceae obtained with the use of an extraction solvent (i.e., a turmeric extract). A turmeric extract is not limited to a solvent extract obtained via extraction with an extraction solvent. A resultant obtained via fractionation or purification such as column chromatography of the solvent extract is also within the scope of the turmeric extract. A turmeric extract used in the present invention can be in the form of an extract after the completion of an extraction procedure (including a fractionation or purification procedure when performed), a concentrate obtained by partially removing a solvent from the extract, or a dry matter obtained by removing a solvent from the extract. A solvent can be removed from an extract by allowing the solvent to evaporate via, for example, heating and/or depression. Methods of heating and depression are not particularly limited. For example, conventional methods can be employed.

The above-described plant material may be, for example, the aforementioned turmeric rhizome. A rhizome of *Curcuma longa* is particularly preferable as the plant material. A rhizome collected from soil may be used. An adequate part of a rhizome may be used in its original form. A part of a rhizome cut into adequate dimensions or configuration may be used. A grounded rhizome may be used. Such plant material may have been dried.

As an extraction solvent, at least one selected from water and a hydrophilic organic solvent can be used. The at least one extraction solvent selected from water and a hydrophilic organic solvent may be any of water, a hydrophilic organic solvent, or a mixed solvent of water and a hydrophilic organic solvent. The hydrophilic organic solvent may also be a mixed solvent of a plurality of hydrophilic organic solvents. The "water" includes hot water. As such hot water, for example, hot water with a temperature of 95° C. or higher can be used. The hydrophilic organic solvent may be, for example, at least one type of alcohol (which may also be a mixed solvent consisting of multiple types of alcohols). The alcohol is not particularly limited, and ethanol is preferable. When a mixed solvent of alcohol and water is used as an extraction solvent, the mixing ratio between alcohol and water is not particularly limited. The mixing ratio is preferably in the range of 10:90 to 90:10, and more preferably in the range of 20:80 to 50:50, for example, at a weight ratio.

Also, supercritical carbon dioxide can be used as an extraction solvent.

A method for obtaining a turmeric extract from a plant material is not particularly limited.

In the present invention, the turmeric extract used is preferably a turmeric extract containing at least one of turmeronol A, turmeronol B and bisacurone, which is extracted with the above-described extraction solvent; and more preferably a turmeric extract containing at least turmeronol A and turmeronol B, which is extracted with the above-described extraction solvent; and further preferably a turmeric extract containing turmeronol A, turmeronol B and bisacurone, which is extracted with the above-described extraction solvent.

Termeronol A and termeronol B are each a compound having a planar structure shown below.

[Formula 1]

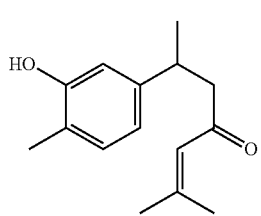

Turmeronol A

[Formula 2]

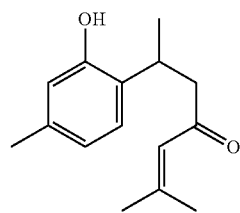

Turmeronol B

In a naturally-occurring substance separated from a turmeric extract, termeronol A and termeronol B are each known to comprise an S configuration at the carbon at position 6 in the partial structure of 2-methyl-2-hepten-4-one. In the present invention, however, it is sufficient if termeronol A and termeronol B each have the planar structure described above, and it may be an S configuration, an R configuration, or a mixture of S and R configurations.

In the present invention, bisacurone is a compound having the following planar structure. Bisacurone has an asymmetric carbon at the position indicated with the symbol * in the planar structure, and may include a plurality of optical isomers. In the present invention, bisacurone may be any optical isomer, or may also be a mixture of two or more types of optical isomers.

[Formula 3]

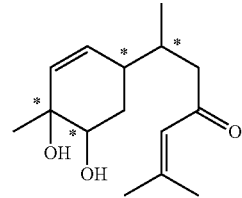

<Turmeronol A, Turmeronol B, and Bisacurone>

At least one of turmeronol A, turmeronol B and bisacurone (hereinafter also referred to as an "active compound"), which is used in the present invention, may be derived from plants, or may also be artificially synthesized. For example, optically active (+)-turmeronol A can be synthesized by the method described in Biosci Biotechnol Biochem. 1993; 57(7): 1137-40.

In the present invention, turmeronol A, turmeronol B and bisacurone may each have the above-described planar structure, or may be any optical isomer, or may also be a mixture of multiple optical isomers.

The active compound used in the present invention is more preferably derived from a plant material, and further preferably derived from a plant of the genus *Curcuma* in the family Zingiberaceae. Specific examples of a plant of the genus *Curcuma* in the family Zingiberaceae and parts thereof are as described above. An active compound can be obtained from a part, such as a rhizome, of a plant of the genus *Curcuma* in the family Zingiberaceae.

An active compound can be extracted from a plant material containing the same. A method of extraction is as described above. An active compound may be in the form of a plant extract and, in particular, a turmeric extract extracted with at least one extraction solvent selected from water and a hydrophilic organic solvent.

Alternatively, a fraction of a highly-purified active compound prepared from a plant extract containing an active compound may be used in the present invention, and such fraction may be integrated into the composition of the present invention. For example, a plant extract containing an active compound may be subjected to liquid-liquid distribution using ethyl acetate/water, and a highly purified active compound can be obtained in an ethyl acetate fraction. Alternatively, a plant extract containing an active compound or a fraction thereof may be subjected to purification via chromatography to obtain a highly-purified active compound. Examples of chromatography techniques that can be employed include reversed-phase column chromatography and normal-phase thin-layer chromatography.

A plant extract containing an active compound or a fraction thereof may be subjected to processing, such as dehydration, pulverization, granulation, or fluidization, in accordance with a conventional technique.

The above-described active compound preferably contains at least turmeronol A and turmeronol B, and more preferably contains turmeronol A, turmeronol B and bisacurone.

<Composition for Improving Vascular Endothelial Function or Improving Blood Flow in Peripheral Blood Vessels>

The composition for improving vascular endothelial function or improving blood flow in peripheral blood vessels of the present invention has an ability to improve vascular endothelial function.

The composition for improving vascular endothelial function or improving blood flow in peripheral blood vessels of the present invention also has an ability to improve blood flow in peripheral blood vessels, a reduction of which causes cold extremities.

Vascular endothelial function means various functions associated with vascular protection, such as a function of releasing various vasoactive substances including nitric oxide (NO), endothelium-derived hyperpolarizing factor (EDHF), and prostaglandin 12 to regulate vascular smooth muscle tension, and a function of suppressing cell adhesion or adhesive aggregation of platelets. Vascular endothelial function can be evaluated by a method of detecting an increase in the plethysmogram of fingertip (=vasodilation) with a probe to measure vasodilator capacity from before avascularization to after the release of avascularization (calculated as RHI (Reactive Hyperemia Index)), a method of measuring the increase percentage of a blood vessel diameter (FMD value (%)) according to a flow-mediated dilation (FMD) after the avascularization of a hand or a foot, a method using strain gauge plethysmography, or the like. Higher RHI and FMD values indicate higher vascular endothelial function. The FMD value can be measured using an ordinary FMD inspection device.

Vascular endothelial function is preferably measured using humans, but it may also be confirmed by in vivo or ex vivo animal tests or using in vitro indexes such as NO productivity of endothelial cells.

Peripheral blood vessels include arterioles, capillaries and venules. Cold extremities are caused by a reduction in the blood flow in the peripheral blood vessels of hands and feet. The term "hand" typically indicates the end part of an arm beyond the wrist, and in particular, it indicates fingers. The term "foot" typically indicates the end part of a lower limb beyond the ankle, and in particular, it indicates toes. The composition for improving vascular endothelial function or improving blood flow in peripheral blood vessels of the present invention improves blood flow in peripheral blood vessels, and in particular, blood flow in the peripheral blood vessels of hands and feet, so as to suppress cold extremities.

The improvement of blood flow in peripheral blood vessels can be evaluated as follows. The feeling of having cold hands or feet is evaluated according to a VAS (Visual Analogue Scale) method, by which the stronger the above-described feeling, the higher the evaluation value that can be obtained. When the evaluation value is reduced, it can be evaluated that blood flow in peripheral blood vessels has been improved.

The composition for improving vascular endothelial function or improving blood flow in peripheral blood vessels of the present invention can be used for preventing or treating diseases such as arteriosclerosis, chronic kidney disease (CKD), hypertension, dyslipidemia, diabetes, obesity/metabolic syndrome, coronary artery disease, cerebrovascular disease, disseminated intravascular coagulation syndrome (DIC), and collagen disease. Also, the composition for improving vascular endothelial function or improving blood flow in peripheral blood vessels of the present invention can be used for preventing or treating the symptom of feeling cold hands and feet. The composition for improving vascular endothelial function or improving blood flow in peripheral blood vessels of the present invention is effective, not only for patients with diabetes or subjects who tend to have obesity, but also for healthy subjects.

The subject of the composition for improving vascular endothelial function or improving blood flow in peripheral blood vessels of the present invention is typically a human. However, the subject of the present composition is not limited to such a human. The subject may also be non-human mammals.

The composition for improving vascular endothelial function or improving blood flow in peripheral blood vessels of the present invention may be in the form of, for example, a pharmaceutical product, a food or beverage product, a feed, a food additive, or a feed additive, and it is preferably in the form of a pharmaceutical product or a food or beverage product. Food or beverage products in the form of, for example, foods with functional claims, foods for specified health use (FOSHU), and nutritional supplements are within the scope of the present invention.

The composition for improving vascular endothelial function or improving blood flow in peripheral blood vessels of the present invention is preferably a composition that is ingested or administered via oral or transnasal administration, and is more preferably a composition that is ingested or administered via oral administration.

In the present invention, the term "daily intake" is used to mean the total amount of the composition of the present invention that is ingested or administered per day, and is used to preferably mean the total amount of the composition of the present invention that is ingested by or administered to one human, in particular, one adult human, per day. As a specific example of the "daily intake" of the composition of the present invention is typically 0.1 g to 500 g of the composition when ingested or administered orally or nasally, and preferably orally. The composition of the present invention may be ingested or administered continuously, or may be ingested or administered when needed.

The form of the composition of the present invention is not particularly limited. For example, it may be a liquid, fluid, gel, semi-solid, or solid form.

The composition of the present invention may further comprise one or more types of other ingredients, in addition to the above-described active compound, the above-described turmeric extract, or the above-described turmeric. The one or more types of other ingredients that may be comprised in the composition of the present invention is not particularly limited. Preferable examples of such other ingredients include ingredients that are acceptable in the final form, such as a pharmaceutical product, a food or beverage product, a feed, a food additive, or a feed additive, and are orally ingestible.

Examples of other ingredients include sweeteners, acidulants, vitamins, minerals, thickeners, emulsifiers, antioxidants, and water. According to need, pigments, aroma chemicals, preservatives, antiseptic agents, fungicides, other physiologically active substances, or the like may be added.

Examples of sweeteners include: monosaccharides and disaccharides, such as glucose, fructose, sucrose, lactose, maltose, palatinose, trehalose, and xylose; isomerized glucose syrup (e.g., glucose-fructose syrup, fructose-glucose syrup, and an isomerized sugar mixture), sugar alcohols (e.g., erythritol, xylitol, lactitol, Palatinit™, sorbitol, and reduced starch syrup), honey, and high-intensity sweeteners (e.g., sucralose, acesulfame potassium, thaumatin, *stevia*, and aspartame).

Examples of acidulants include citric acid, malic acid, gluconic acid, tartaric acid, lactic acid, phosphoric acid, and salts thereof. Each of such substances can be used alone or two or more thereof can be used in combination.

Examples of vitamins include vitamin A, vitamin B1, vitamin B2, vitamin B6, vitamin E, niacin, and inositol.

Examples of minerals include calcium, magnesium, zinc, and iron.

Examples of thickeners include carrageenan, gellan gum, xanthan gum, gum Arabic, tamarind gum, guar gum, Locust bean gum, karaya gum, agar, gelatin, pectin, soybean polysaccharides, and carboxymethyl cellulose (CMC).

Examples of emulsifiers include glycerin fatty acid ester, sucrose fatty acid ester, sorbitan fatty acid ester, lecithin, plant sterol, and saponin.

Examples of antioxidants include vitamin C, tocopherol (vitamin E), and enzyme-treated rutin.

The other ingredients can be adequately incorporated in adequate amounts that a person skilled in the art generally employs for food or beverage, pharmaceutical, or other compositions.

The formulation of the compound integrated with one or more other ingredients formulated by an adequate means may be in the form of a solid composition, such as powder, granules, capsules, and tablets (including coated tablets such as sugar-coated tablets, multilayer tablets, orally disintegrating tablets, and chewable tablets), or a liquid composition such as a solution.

<Composition for Improving Vascular Endothelial Function or Improving Blood Flow in Peripheral Blood Vessels, Comprising, as an Active Ingredient, at Least One of Turmeronol A, Turmeronol B and Bisacurone>

A first aspect of the composition of the present invention relates to a composition for improving vascular endothelial function or improving blood flow in peripheral blood vessels, comprising, as an active ingredient, at least one of turmeronol A, turmeronol B and bisacurone. This composition may also be referred to as "the composition according to the first aspect of the present invention" in the following description in some cases.

The content of the above-described active compound or the above-described turmeric extract containing the same in the composition according to the first aspect of the present invention is not particularly limited, as long as it is the content that is effective for the improvement of vascular endothelial function and/or the improvement of blood flow in peripheral blood vessels.

The composition according to the first aspect of the present invention comprises preferably 20 µg or more, more preferably 37 µg or more, particularly preferably 55 µg or more, further preferably 74 µg or more, and most preferably 100 µg or more turmeronol A and turmeronol B in total per daily intake. In this case, the composition according to the first aspect of the present invention has particularly high effect of enhancing or improving vascular endothelial function, and/or particularly high effect of promoting blood flow in peripheral blood vessels. The upper limit of the total content of turmeronol A and turmeronol B is not particularly limited, and the composition according to the first aspect of the present invention comprises typically 1100 µg or less, preferably 550 µg or less, more preferably 330 µg or less, particularly preferably 220 µg or less, further preferably 170 µg or less, and most preferably 125 µg or less turmeronol A and turmeronol B in total per daily intake. When the composition according to the first aspect of the present invention comprises at least one of turmeronol A and turmeronol B in the form of a turmeric extract containing the at least one compound, the composition preferably comprises the turmeric extract, such that the total amount of turmeronol A and turmeronol B can be set within the above-described range.

The composition according to the first aspect of the present invention comprises preferably 17 µg or more, more preferably 28 µg or more, particularly preferably 43 µg or more, further preferably 57 µg or more, and most preferably 77 µg or more turmeronol A per daily intake. In this case, the composition according to the first aspect of the present invention has particularly high effect of enhancing or improving vascular endothelial function, and/or particularly high effect of promoting blood flow in peripheral blood vessels. The upper limit of the content of turmeronol A is not particularly limited, and the composition according to the first aspect of the present invention comprises typically 900 µg or less, preferably 430 µg or less, more preferably 260 µg or less, particularly preferably 175 µg or less, further preferably 130 µg or less, and most preferably 95 µg or less turmeronol A per daily intake. When the composition according to the first aspect of the present invention comprises turmeronol A in the form of a turmeric extract containing the turmeronol A, the composition preferably comprises the turmeric extract, such that the amount of turmeronol A can be set within the above-described range.

The composition according to the first aspect of the present invention comprises preferably 5 µg or more, more preferably 8 µg or more, particularly preferably 12 µg or more, further preferably 16 µg or more, and most preferably 22 µg or more turmeronol B per daily intake. In this case, the composition according to the first aspect of the present invention has particularly high effect of enhancing or improving vascular endothelial function, and/or particularly high effect of promoting blood flow in peripheral blood vessels. The upper limit of the content of turmeronol B is not particularly limited, and the composition according to the first aspect of the present invention comprises typically 250 µg or less, preferably 123 µg or less, more preferably 74 µg or less, particularly preferably 50 ng or less, further preferably 37 µg or less, and most preferably 27 µg or less turmeronol B per daily intake. When the composition according to the first aspect of the present invention comprises turmeronol B in the form of a turmeric extract containing the turmeronol B, the composition preferably comprises the turmeric extract, such that the amount of turmeronol B can be set within the above-described range.

The composition according to the first aspect of the present invention comprises preferably 80 µg or more, more preferably 133 µg or more, particularly preferably 200 µg or more, further preferably 267 µg or more, and most preferably 360 µg or more bisacurone per daily intake. In this case, the composition according to the first aspect of the present invention has particularly high effect of enhancing or improving vascular endothelial function, and/or particularly high effect of promoting blood flow in peripheral blood vessels. The upper limit of the content of bisacurone is not particularly limited, and the composition according to the first aspect of the present invention comprises typically 4000 µg or less, preferably 2000 µg or less, more preferably 1200 µg or less, particularly preferably 800 µg or less, further preferably 600 µg or less, and most preferably 440 µg or less bisacurone per daily intake. When the composition according to the first aspect of the present invention comprises bisacurone in the form of a turmeric extract containing the bisacurone, the composition preferably comprises the turmeric extract, such that the amount of bisacurone can be set within the above-described range.

In the composition according to the first aspect of the present invention, the content of curcumin is typically less than 30 mg, preferably 5 mg or less, more preferably 2.5 mg or less, particularly preferably 1.5 mg or less, further preferably 1 mg or less, still further preferably 700 µg or less, and most preferably 520 µg or less per daily intake. In this case, the composition according to the first aspect of the present invention has particularly high effect of enhancing or improving vascular endothelial function, and/or particularly high effect of promoting blood flow in peripheral blood vessels. It may be adequate even if the composition according to the first aspect of the present invention does not comprise curcumin, but the composition according to the first aspect of the present invention comprises typically 94 µg or more, preferably 157 µg or more, more preferably 235 µg or more, particularly preferably 314 µg or more, and most preferably 423 µg or more curcumin per daily intake. When the composition according to the first aspect of the present invention comprises at least one of turmeronol A, turmeronol B and bisacurone in the form of a turmeric extract containing the at least one compound, the composition preferably comprises the turmeric extract, such that the amount of curcumin can be set within the above-described range.

The composition according to the first aspect of the present invention is preferably a composition that is continuously ingested. Specifically, the present composition is continuously ingested at a frequency of once or twice or more per day, preferably over 4 weeks or more, more preferably over 8 weeks or more, and most preferably over 12 weeks or more.

The composition according to the first aspect of the present invention may be the above-described active compound per se or the above-described turmeric extract itself containing the same, or may also be a composition comprising the above-described active compound or the above-described turmeric extract containing the same and at least one type of other ingredients. When the composition of the present invention comprises the above-described active compound or the above-described turmeric extract containing the same and at least one type of other ingredients, the composition may be in the form of a composition of the above-described active compound or the above-described turmeric extract containing the same mixed with one or more other ingredients, a formulation of the active compound or the turmeric extract containing the same integrated with one or more other ingredients formulated by an adequate means, or a composition of the formulation of the active compound or the turmeric extract containing the same integrated with one or more other ingredients further mixed with other ingredients.

<Composition for Improving Vascular Endothelial Function or Improving Blood Flow in Peripheral Blood Vessels, Comprising Turmeric as Active Ingredient>

A second aspect of the composition of the present invention relates to a composition for improving vascular endothelial function or improving blood flow in peripheral blood vessels, comprising a turmeric as an active ingredient. However, the scope of the composition for improving vascular endothelial function or improving blood flow in peripheral blood vessels according to the second aspect of the present invention excludes a composition comprising a clove, a coriander, a cumin, a garlic, a ginger, an onion and a red pepper, in addition to a turmeric, and a composition further comprising a garlic in addition to a turmeric. This composition may also be referred to as "the composition according to the second aspect of the present invention" in the following description in some cases.

The content of the turmeric in the composition according to the second aspect of the present invention is not particularly limited, as long as it is the content that is effective for the improvement of vascular endothelial function and/or the improvement of blood flow in peripheral blood vessels.

The composition according to the second aspect of the present invention is preferably a composition that is continuously ingested. Specifically, the present composition is continuously ingested at a frequency of once or twice or more per day, preferably over 4 weeks or more, more preferably over 8 weeks or more, and most preferably over 12 weeks or more.

The composition according to the second aspect of the present invention may be a turmeric per se, or may also be a composition comprising such a turmeric and at least one type of other ingredients.

<Method for Improving Vascular Endothelial Function by Administration of at Least One of Turmeronol a, Turmeronol B and Bisacurone>

A further aspect of the present invention relates to a method for improving vascular endothelial function, comprising:

administering at least one of turmeronol A, turmeronol B and bisacurone, or a turmeric extract containing at least one of turmeronol A, turmeronol B and bisacurone, which is extracted with at least one extraction solvent selected from water and a hydrophilic organic solvent, to a subject in need of improving vascular endothelial function; and improving the vascular endothelial function in the subject.

The active compound or the turmeric extract used in the method according to the present aspect can be in the aforementioned form of the composition of the present invention.

The subject in the method according to the present aspect is typically a human. The subject may also be non-human mammals.

In the method according to the present aspect, the administration route is preferably oral or intranasal administration, and is particularly preferably oral administration.

In the method according to the present aspect, the amount of the active compound or the turmeric extract administered to a subject is not particularly limited, as long as it is an amount effective for the improvement of vascular endothelial function. For example, in one embodiment, when the subject is an adult, it is preferable to administer the active compound or the turmeric extract to the subject, so that 20 µg or more turmeronol A and turmeronol B in total can be administered to the subject at a daily dose. In another embodiment, when the subject of an adult, it is preferable to administer the active compound or the turmeric extract to the subject, so that 17 µg or more turmeronol A can be administered to the subject per day. In another embodiment, when the subject of an adult, it is preferable to administer the active compound or the turmeric extract to the subject, so that 5 µg or more turmeronol B can be administered to the subject per day. In another embodiment, when the subject of an adult, it is preferable to administer the active compound or the turmeric extract to the subject, so that 80 µg or more bisacurone can be administered to the subject per day.

Further, it is preferable to administer the active compound or the turmeric extract to the subject, so that the amount of curcumin administered per day can be less than 30 mg. Further preferably, it is preferable to administer the active compound or the turmeric extract to the subject, so that each active compound can be administered to the subject at an amount that is described as a preferred amount of the active compound in the daily intake of the composition according to the first aspect of the present invention.

<Method for Improving Vascular Endothelial Function by Administration of Turmeric>

A further aspect of the present invention relates to a method for improving vascular endothelial function, comprising:

administering a turmeric to a subject in need of improving vascular endothelial function; and improving the vascular endothelial function in the subject (provided that the turmeric is not combined with a clove, a coriander, a cumin, a garlic, a ginger, an onion and a red pepper, and is not combined, either, with a garlic).

The turmeric used in the method according to the present aspect can be in the aforementioned form of the composition of the present invention.

The subject in the method according to the present aspect is typically a human. The subject may also be non-human mammals.

In the method according to the present aspect, the administration route is preferably oral or intranasal administration, and is particularly preferably oral administration.

<Method for Improving Blood Flow in Peripheral Blood Vessels by Administration of at Least One of Turmeronol A, Turmeronol B and Bisacurone>

A further aspect of the present invention relates to a method for improving blood flow in peripheral blood vessels, comprising:

administering at least one of turmeronol A, turmeronol B and bisacurone, or a turmeric extract containing at least one of turmeronol A, turmeronol B and bisacurone, which is extracted with at least one extraction solvent selected from water and a hydrophilic organic solvent, to a subject in need of improving blood flow in peripheral blood vessels; and improving the blood flow in peripheral blood vessels in the subject.

The active compound or the turmeric extract used in the method according to the present aspect can be in the aforementioned form of the composition of the present invention.

The subject in the method according to the present aspect is typically a human. The subject may also be non-human mammals.

In the method according to the present aspect, the administration route is preferably oral or intranasal administration, and is particularly preferably oral administration.

In the method according to the present aspect, the amount of the active compound or the turmeric extract administered to a subject is not particularly limited, as long as it is an amount effective for the improvement of blood flow in peripheral blood vessels. For example, in one embodiment, when the subject is an adult, it is preferable to administer the active compound or the turmeric extract to the subject, so that 20 µg or more turmeronol A and turmeronol B in total can be administered to the subject at a daily dose. In another embodiment, when the subject of an adult, it is preferable to administer the active compound or the turmeric extract to the subject, so that 17 µg or more turmeronol A can be administered to the subject per day. In another embodiment, when the subject of an adult, it is preferable to administer the active compound or the turmeric extract to the subject, so that 5 µg or more turmeronol B can be administered to the subject per day. In another embodiment, when the subject of an adult, it is preferable to administer the active compound or the turmeric extract to the subject, so that 80 µg or more bisacurone can be administered to the subject per day. Further, it is preferable to administer the active compound or the turmeric extract to the subject, so that the amount of curcumin administered per day can be less than 30 mg. Further preferably, it is preferable to administer the active compound or the turmeric extract to the subject, so that each active compound can be administered to the subject at a weight that is described as a preferred amount of the active compound in the daily intake of the composition according to the first aspect of the present invention.

<Method for Improving Blood Flow in Peripheral Blood Vessels by Administration of Turmeric>

A further aspect of the present invention relates to a method for improving blood flow in peripheral blood vessels, comprising:

administering a turmeric to a subject in need of improving blood flow in peripheral blood vessels; and improving the blood flow in peripheral blood vessels in the subject (provided that the turmeric is not combined with a clove, a coriander, a cumin, a garlic, a ginger, an onion and a red pepper, and is not combined, either, with a garlic).

The turmeric used in the method according to the present aspect can be in the aforementioned form of the composition of the present invention.

The subject in the method according to the present aspect is typically a human. The subject may also be non-human mammals.

In the method according to the present aspect, the administration route is preferably oral or intranasal administration, and is particularly preferably oral administration.

Examples

1. Method for Production of Turmeric Extract

A turmeric extract was prepared by extracting the rhizome part of turmeric (*Curcuma longa*) with water, and heat-drying the extract under a reduced pressure to remove water. The amounts of turmeronol A (TA) and turmeronol B (TB) in the turmeric extract were measured using LC/MS. The amounts of bisacurone and curcumin were measured using HPLC.

2. Test Food

The test food was a tablet comprising a turmeric extract containing, per three tablets, 86.5 µg of TA, 24.7 µg of TB, 400 µg of bisacurone and 471 µg of curcumin. The tablet was prepared by mixing the turmeric extract, an excipient, a lubricant, a coloring agent, and other ingredients for manufacturing (fine grain silicon dioxide and sucrose fatty acid ester), followed by tablet-making.

The placebo food was a tablet prepared by replacing the turmeric extract comprised in the above-described test food with an excipient.

3. Method for Measuring Vascular Endothelial Function

It has been known that when blood flow in blood vessels is blocked (avascularization) and then the avascularization is released, vasodilator substances such as nitrogen oxide (NO) are secreted from vascular endothelial cells upon recanalization, so that vasodilation occurs. As the scale of the vasodilation reaction due to the release of the avascularization increases, the vascular endothelial function is better. On the other hand, if vascular endothelial function disorder occurs, the vasodilation reaction decreases.

RH-PAT (Reactive Hyperemia Peripheral Arterial Tonometry) is a method of examining vasodilator capacity from before avascularization to after the release of the avascularization (which is calculated as RHI (Reactive Hyperemia Index)), by detecting an increase in the plethysmogram of fingertips (=vasodilation) with probes. Higher RHI value indicates better vascular endothelial function. In the present example, for the measurement of the RHI, Endo-PAT2000 (manufactured by Etamar Medical) was used (References: Endo-PAT2000 Catalog "Endo-Pat2000—Star Product," http://www.starprod.co.jp/products/pdf/firstaid_ward_15.pdf, Seigo SUGIYAMA" Evaluation of vascular endothelial function by reactive hyperemia peripheral arterial tonometry (RH-PAT)," Heart, Vol. 46 No. 10 (2014)).

The measurement of RHI was carried out by the following method. The upper arm of a subject lying on the back was wrapped with a vascular pressurization cuff, and probes were then installed on the fingertips of both hands. The volume pulse wave before avascularization was measured for 2 minutes 30 seconds. The cuff wrapped around the arm was pressurized, so that avascularization was performed for 5 minutes. Thereafter, the pressurization with the cuff was released, and an increase the volume pulse wave after the release of the avascularization (vasodilation) was measured for 1 minute. From the results of the pulse wave before avascularization (baseline) and the pulse wave after the avascularization, RHI indicating vascular endothelial function was calculated.

4. Evaluation Test of Vascular Endothelial Function

Twenty-one male and female human subjects with an age of 50 to 69, who had a systolic blood pressure of 101 to 119 mmHg (optimal systolic blood pressure), were randomly assigned into two groups (placebo group: 10 subjects; and turmeric extract group: 11 subjects). Thereafter, under a double blind test, a test food containing a turmeric extract or a placebo food not containing such a turmeric extract was ingested by the subjects once a day (three tablets each day) before supper for 12 weeks. Vascular endothelial function (RHI) was measured before ingestion of the test food and 12 weeks after the ingestion. FIG. 1 shows the results regarding the amount of change (ΔRHI) in the RHI from before the intake of the test food to 12 weeks after the intake of the test food. As shown in FIG. 1, the amount of change (ΔRHI) in the RHI of the turmeric extract group was significantly higher than that of the placebo group. From these results, it became clear that the intake of a turmeric extract improves vascular endothelial function.

5. Evaluation Method of Blood Flow (Cold Extremities)

Cold extremities were evaluated according to a VAS (Visual Analogue Scale) method.

The VAS method is an inspection of digitizing the degree of subjective symptoms and evaluating it. According to the VAS method, the left end of a straight line (0 point) is defined to be a state in which a subject does not feel the concerned mood/sense at all, and the right end (100 points) is defined to be a state in which a subject feels the concerned mood/sense most strongly in the subject's experience. Then, the subjects are asked to show the degree of their subjective symptoms on the line. This method has been widely used for subjective evaluation also in clinical medicine, and in particular, this method is used in comparison of the conditions of a single subject before and after administration of a drug, etc.

6. Evaluation Test of Blood Flow (Cold Extremities)

Eighty-seven male and female human subjects with an age of 50 to 69 were randomly assigned into two groups (placebo group: 44 subjects; and turmeric extract group: 43 subjects). Thereafter, under a double blind test, a test food containing a turmeric extract or a placebo food not containing such a turmeric extract was ingested by the subjects once a day (three tablets per day) before supper for 12 weeks. Cold extremities were measured according to the VAS method before the intake of the test food, 4 weeks after the intake, 8 weeks after the intake, and 12 weeks after the intake.

Figure 2:
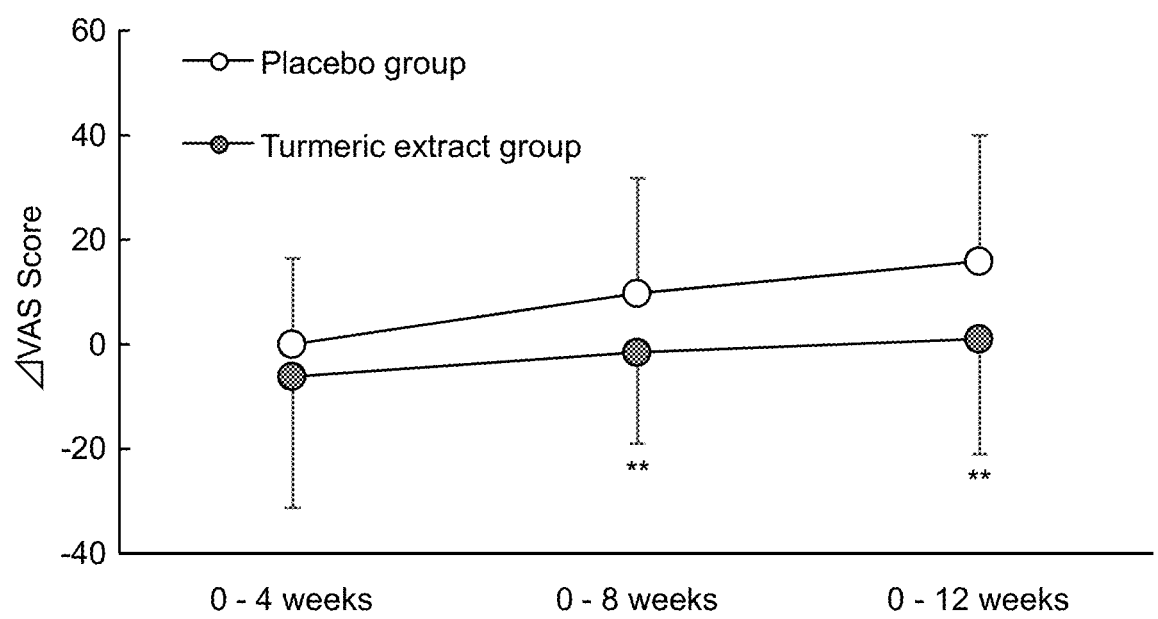
FIG. 2 shows the amount of change (ΔVAS Score) in the evaluation values of cold extremities according to a VAS method from before the intake of a test food (a turmeric extract group or a placebo group) to 4 weeks, 8 weeks and 12 weeks after the intake of the test food.

FIG. 2 shows the results regarding the amount of change (ΔVAS Score) in the cold extremities from before the intake of the test food to 4, 8, and 12 weeks after the intake of the test food. As shown in FIG. 2, the amounts of change in the cold extremities of the turmeric extract group at 8 weeks and 12 weeks after the intake of the test food were significantly lower than those of the placebo group. From these results, it became clear that the intake of a turmeric extract improves blood flow and suppresses cold extremities.

All publications, patents and patent applications cited in the present description are incorporated herein by reference in their entirety.

The invention claimed is:

1. A method for improving blood flow in peripheral blood vessels, comprising:
    administering at least one of turmeronol A, turmeronol B and bisacurone to a subject in need of improving blood flow in peripheral blood vessels to suppress cold extremities; and
    improving the blood flow in peripheral blood vessels in the subject,
    wherein the administration comprises administering 20 μg or more turmeronol A and turmeronol B in total to the subject per day.

2. A method for improving blood flow in peripheral blood vessels, comprising:
    administering at least one of turmeronol A, turmeronol B and bisacurone to a subject in need of improving blood flow in peripheral blood vessels to suppress cold extremities; and
    improving the blood flow in peripheral blood vessels in the subject,
    wherein the administration comprises administering 17 μg or more turmeronol A to the subject per day.

3. A method for improving blood flow in peripheral blood vessels, comprising:
    administering at least one of turmeronol A, turmeronol B and bisacurone to a subject in need of improving blood flow in peripheral blood vessels to suppress cold extremities; and
    improving the blood flow in peripheral blood vessels in the subject,
    wherein the administration comprises administering 5 μg or more turmeronol B to the subject per day.

4. A method for improving blood flow in peripheral blood vessels, comprising:
    administering at least one of turmeronol A, turmeronol B and bisacurone to a subject in need of improving blood flow in peripheral blood vessels to suppress cold extremities; and
    improving the blood flow in peripheral blood vessels in the subject,
    wherein the administration comprises administering 80 μg or more bisacurone to the subject per day.

5. A method for improving blood flow in peripheral blood vessels, comprising:
- administering at least one of turmeronol A, turmeronol B and bisacurone to a subject in need of improving blood flow in peripheral blood vessels to suppress cold extremities; and
- improving the blood flow in peripheral blood vessels in the subject,
- wherein the administration comprises administering less than 30 mg of curcumin to the subject per day.

* * * * *